US005827647A

United States Patent [19]

Young et al.

[11] Patent Number: 5,827,647

[45] Date of Patent: Oct. 27, 1998

[54] PARVOVIRUS CAPSIDS

[75] Inventors: Neal S. Young, Washington, D.C.; Sachiko Kajigaya, Rockville; Takashi Shimada, Bethseda, both of Md.

[73] Assignee: The United States of America as represented by the Department of Health and Human Services, Washington, D.C.

[21] Appl. No.: 463,332

[22] Filed: Jun. 5, 1995

Related U.S. Application Data

[60] Division of Ser. No. 612,672, Nov. 14, 1990, Pat. No. 5,508,186, which is a continuation-in-part of Ser. No. 270,098, Nov. 14, 1988, abandoned.

[51] Int. Cl.[6] .......... C12Q 1/70

[52] U.S. Cl. .......... 435/5; 435/235.1

[58] Field of Search .......... 435/5, 235.1

[56] References Cited

U.S. PATENT DOCUMENTS 5,508,168 4/1996 Young et al. .......... 435/235.1

FOREIGN PATENT DOCUMENTS 880202 3/1988 WIPO .

OTHER PUBLICATIONS

Stierle, G. et al. Ann Rheum. Dis. vol. 46, No. 3, pp. 219–223 (abstract only cited), 1987.

Fridell, E. et al. Scand. J. Infect. Dis. vol. 21, No. 6, pp. 597–603 (abstract only cited), 1989.

Brown, C. et al. Virus Res., vol. 15, No. 3, pp. 197–212, 1990.

*Primary Examiner*—Mary E. Mosher
*Attorney, Agent, or Firm*—Morgan & Finnegan, L.L.P.

[57] ABSTRACT

The present invention relates to a method of producing non-infectious-parvovirus capsids and to diagnostic assays and vaccines utilizing same. The invention further relates to recombinant baculoviruses encoding parvovirus structural proteins and host cells infected therewith. The invention also relates to a method of packaging and delivering genetic information utilizing the noninfectious capsids.

6 Claims, 17 Drawing Sheets

Human DHFR Minigene DM14

```
                    vector  |  insert
pVP1/941  G C G G A T C T T G T A G A T T A T G A G T A A A
                                         Met Ser Lys
pVP2/941  G C G G A T C C A T G A C T T C A G T T A A T
                              Met Thr Ser Val Asn
```

Lane 7

(Infection rate 1: 1/100)

$\bar{V}$P 1 : 29.4%
$\bar{V}$P 2 : 70.6%

Lane 8

(Infection rate 1: 1/10)

$\bar{V}$P 1 : 20.0%
$\bar{V}$P 2 : 80%

Lane 6

(Infection rate 1: 1)

$\bar{V}$P 1 : 7.1%
$\bar{V}$P 2 : 92.9%

PARVOVIRUS CAPSIDS

This application is a divisional application of Ser. No. 07/612,672, filed Nov. 14, 1990, now U.S. Pat. No. 5,508,186, which is a continuation-in-part of application Ser. No. 07/270,098, filed Nov. 14, 1988, now abandoned, all of which are hereby incorporated in their entirety by reference.

BACKGROUND OF THE INVENTION

1. Technical Field

The present invention relates, in general, to a method of producing parvovirus antigens, and in particular, to a method of producing empty, and thus non-infectious, parvovirus capsids, and to diagnostic assays and vaccines utilizing same. The invention also relates to a method of packaging and delivering genetic information using the empty parvovirus capsids. The invention further relates to a method of packing and delivering nonparvovirus proteins, such as other antigens, ligands and enzymes, using empty parvovirus capsids.

2. Background Information

Parvoviruses are common agents of animal disease. The first strong link between parvovirus infection and human disease came from the serendipitous discovery in 1975 of parvovirus-like particles in the sera of normal human blood donors (one of the samples having been designated B19). Since that time, B19 parvovirus has been identified as the causative agent of: i) transient aplastic crisis (TAC) of hemolytic disease, ii) the common childhood exanthem called fifth disease; iii) a polyarthralgia syndrome in normal adults that may be chronic and resembles in its clinical features, rheumatoid arthritis; iv) some cases of chronic anemia and/or neutropenia; and v) some cases of hydrops fetalis. The entire spectrum of human illness caused by parvoviruses, however, is not yet clear due, in large part, to the fact that an appropriate assay is not widely available.

Parvoviruses require replicating cells for propagation, and parvovirus infection, therefore, results in pathologic changes in mitotically active host tissue. In infected children and adults, B19 parvovirus replicates in the bone marrow; in the fetus, B19 parvovirus replicates in the liver, there a hematopoietic organ. Erythroid progenitor cells are the only cell type known to be subject to infection by this virus.

The limited host and tissue range of B19 parvovirus has hampered the development of assays specific for the virus. Since the discovery of the virus, the quantity of B19 antigen available as a reagent has been limited to that obtainable from sera fortuitously obtained from infected patients. The virus has an extraordinary tropism for human erythroid progenitor cells and has only been propagated in human bone marrow cell cultures (Ozawa et al. Science 233:883 (1986)), fetal liver (Yaegashi et al. *J. Virol.* 63:2422 (1989)) and, to a much lesser degree, in erythroleukemia cells (Takahashi et al. *J. Inf. Dis.* 160:548 (1989)). The bone marrow cultures, however, require explanted bone marrow cells and, therefore, are not practical for virus propagation. The development of and availability of clinical assays continue to be limited by the availability of the antigen. The production of stable transformants capable of producing B19 protein products has been prevented by the fact that some of these products are lethal to transfected cells.

SUMMARY OF THE INVENTION

It is a general object of the invention to provide a method of producing large quantities of parvovirus antigens.

It is a specific object of the invention to provide a method of effecting the expression of parvovirus structural proteins in cell culture.

It is another object of the invention to provide non-infectious parvovirus capsids.

It is a further object of the invention to provide a safe and effective method of producing antibodies against parvovirus capsid proteins.

It is a still further object of the invention to provide a vaccine effective against parvovirus infection.

It is another object of that invention to provide diagnostic assays for detecting the presence in biological samples of parvovirus particles or antibodies thereto.

It is a further object of the invention to provide a method of treating hemoglobinopathies, enzyme deficiency states and other diseases that may be amenable to genetic therapy.

It is another object of the present invention to provide a method of presenting antigens, ligands and enzymes utilizing the parvovirus capsids.

Further objects will be clear to one skilled in the art from the following detailed description of the present invention.

In one embodiment, the present invention relates to a method of producing parvovirus capsids comprising the steps of:

i) introducing into a host cell a recombinant DNA molecule comprising:

a) an expression vector, and b) a DNA sequence encoding the structural proteins of a parvovirus, with the proviso that genes encoding non-structural parvovirus protein are not included in the DNA sequence;

ii) culturing the cells under conditions such that the structural proteins are produced and self assemble to form the capsids; and iii) isolating the capsids.

In another embodiment, the present invention relates to a parvovirus antigen consisting essentially of a parvovirus capsid.

In a further embodiment, the present invention relates to a parvovirus antigen consisting essentially of a parvovirus capsid of major structural proteins free of minor structural proteins.

In yet another embodiment, the present invention relates to a diagnostic assay for parvovirus infection comprising:

i) contacting a sample from a patient suspected of being infected with parvovirus with the above-described parvovirus capsid, and ii) detecting the formation of a complex between anti-parvovirus antibodies present in the sample and the parvovirus capsid.

In another embodiment, the present invention relates to an anti-parvovirus vaccine comprising the above-described parvovirus capsid and a pharmaceutically acceptable carrier.

In another embodiment, the invention relates to a method of packaging and transferring genetic information comprising i) encapsidating the genetic information in the above-described parvovirus capsid and ii) introducing the encapsidated information into a host cell.

In yet another embodiment, the present invention relates to a diagnostic kit comprising:

i) the above-described parvovirus capsid; and ii) ancillary reagents.

In a further embodiment, the present invention relates to a recombinant baculovirus comprising a DNA segment encoding a minor structural protein of a parvovirus and to a recombinant baculovirus comprising a DNA segment encoding a major structural protein of a parvovirus.

In another embodiment, the present invention relates to a method of producing parvovirus capsids comprising the steps of:

i) infecting an insect cell with the recombinant baculovirus encoding the major structural protein or co-infecting an insect cell with both of the above-described recombinant baculoviruses;

ii) culturing the cells under conditions such that the major structural proteins are produced and self assemble to form the capsids; and iii) isolating the capsids.

In yet a further embodiment, the present invention relates to a method of producing a protein presenting capsid comprising the steps of:

i) coinfecting an insect cell with (a) a first recombinant baculovirus encoding a major structural parvovirus protein and (b) a second recombinant baculovirus encoding the nonunique region of a minor structural parvovirus protein and a nonparvovirus protein;

ii) culturing the cells under conditions such that the expressed proteins self assemble to form the capsids; and iii) isolating the capsids.

In another embodiment, the present invention relates to a protein presenting capsid comprising a major structural parvovirus protein and a nonunique region of a minor structural parvovirus protein joined to a nonparvovirus protein.

BRIEF DESCRIPTION OF THE DRAWINGS

FIG. 5A—control CHO cells, and FIG. 5B transformed CHO cells.

FIGS. 10A-1, 10A-2, 10A-3, 10B, 10C. Expression of B19 parvovirus proteins in insect cells infected with recombinant baculoviruses. (A) Immunofluorescence of Sf9 cells infected with pVP1/941 (a), pVP2/941 (b), and wild type baculovirus (c) after staining with convalescent phase antiserum to B19 parvovirus (x 1500). (B) Immunoblot of lysates from cells infected with pVP1/941 (a), pVP2/941 (b) both pVP1/941 and pVP2/941 (c), and wild type baculovirus after development with convalescent phase antiserum followed by $^{125}$I-labeled protein A. (C) Coomassie blue dye-stained polyacrylamide gel of Sf9 cell lysates after infection with recombinant baculovirus pVP1/941 (a), pVP2/941 (b), both pVP1/941 and pVP2/941 (c), and wild type baculovirus (d).

DETAILED DESCRIPTION OF THE INVENTION

Figure 1:
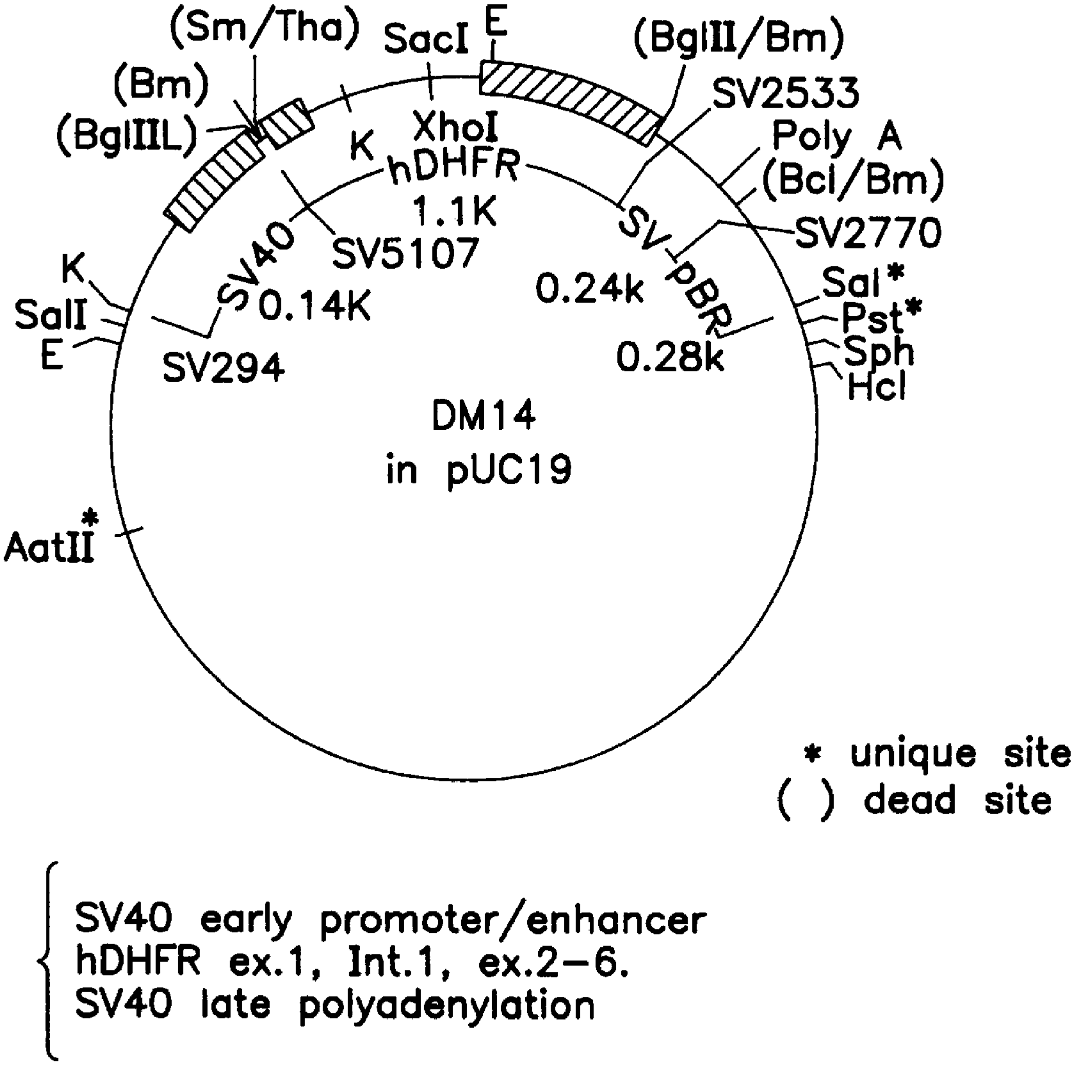
FIG. 1. Human DHFR minigene DM14.

The present invention relates to a method of producing parvovirus structural proteins utilizing recombinant DNA techniques, to expression vectors containing DNA sequences encoding the structural proteins, and to cells transformed with such recombinant molecules. The present invention also relates to recombinant baculoviruses encoding parvovirus structural proteins and to insect cells infected with such recombinant viruses. The invention further relates to diagnostic assays utilizing the recombinantly produced parvovirus protein products, or antibodies to such proteins. The invention also relates to a vaccine effective against parvoviral infection comprising the recombinantly produced viral protein product. The invention further relates to methods of treating diseases amenable to genetic therapy, i.e., hemoglobinopathies and enzyme deficiency states, utilizing the recombinantly produced parvovirus protein products, specifically parvoviral capsids, in cell transfections. The present invention further relates to methods of producing protein presenting capsid vehicles.

The present invention developed from Applicants' discovery that empty, and thus non-infectious, parvovirus capsids can be produced from the major and minor parvovirus capsid protein species or from the major parvovirus capsid protein species alone, without the non-structural proteins. (The minor structural protein alone can not form a capsid.) The elimination of the noncapsid proteins allows for the production of parvoviral particles, microscopically indistinguishable from infectious particles, which are incapable of killing the host cell.

In one embodiment, the present invention relates to a method of producing parvovirus structural proteins, for example, B19 structural proteins, utilizing recombinant DNA techniques. Advantageously, the structural proteins self assemble in the host cell (eucaryotic or procaryotic) to form an empty, but intact, parvoviral capsid. Quantities of parvovirus capsids equal to or greater than those present in infected bone marrow cells, can be produced by the method of the invention.

In a preferred embodiment, eucaryotic cells are transfected with a recombinant DNA molecule comprising an expression vector and the coding sequences of either the major capsid protein or the major and minor capsid proteins of a parvovirus, under control of a promoter. For selection, cells carrying a marker that alters the phenotype of the cell are used as the host. The recombinant DNA molecule containing the capsid-encoding sequences is cotransfected with the sequence encoding the marker gene (i.e., a gene encoding an enzyme deficient in the untransfected cell). Transformants having the appropriate phenotype are readily selected by growing the cells in a selective medium. (Cells can be selected positively or negatively; negatively by the presence of a gene conferring resistance in selective medium and positively by the expression of a detectable marker allowing for identification and isolation of positive cells.) Such transformants are then screened, using known techniques, to determine which contain the capsid proteins. The capsid proteins are isolated in substantially pure form using protocols known in the art.

In a most preferred embodiment, CHO cells deficient in dihydrofolate reductase (DHFR) are cotransfected with: i) a recombinant DNA molecule comprising an expression vector and a DNA sequence encoding the two B19 parvovirus capsid proteins driven by the strong single B19 promoter, and ii) a human DHFR minigene driven by the SV40 early promoter enhancer unit. Transformants bearing the DHFR+ phenotype are selected by growing the cells in a medium lacking nucleosides; colonies are screened by RNA Northern analysis for expression of B19 genes. Coamplification of the integrated B19 capsid-encoding sequence and the DHFR sequence can be accomplished by treating the cells with increasing concentrations of methotrexate; coamplification results in detectable levels of protein expression.

Empty B19 parvovirus capsids are found in the nuclei and cytosol of the CHO cells transfected and cultivated as described above. Large quantities of capsids are not released into the culture supernatants. The expression of the empty capsids does not affect growth of the CHO cells.

In another embodiment, the present invention relates to a method of producing parvovirus capsids utilizing baculoviruses, for example, Autographa california nuclear polyhedrosis virus. Capsids composed of the major and the minor structural proteins and capsids composed of the major structural protein alone are produced. The resulting capsids are suitable reagents for human use and are easy to produce and purify.

In a preferred embodiment, recombinant baculoviruses are produced which encode the major structural parvovirus protein, the minor structural parvovirus protein, or a fusion protein. To form an empty, but intact parvovirus capsid containing the major and the minor structural proteins, host insect cells (for example, Spodoptera frugiperda cells) are either infected with recombinant baculoviruses encoding both structural proteins or are coinfected with recombinant baculoviruses encoding the major protein species and recombinant baculoviruses encoding the minor protein species. Preferably, the cells are infected with viruses at a multiplicity of infections ranging from 10 to 50. The infected cells are cultured and the capsids self assemble. The assembled capsids are isolated therefrom. Capsids composed of only the major structural protein are produced by infecting insect cells with recombinant baculoviruses encoding the major protein.

That capsids, morphologically indistinguishable from natural empty capsids, assemble from the major parvovirus structural protein, VP2, alone was unexpected. In computer modeling, VP1, the minor parvovirus structural protein species, has been proposed as an internal protein that stabilized the capsid structure (Parvoviridae, *In Animal Virus Structure* ed. Nermut and Steven, Elsevier, New York 325–334 (1987)). The present data indicate instead that the minor structural protein is not required for capsid assembly; in fact, the minor structural protein alone is incapable of forming a capsid structure. Several pieces of data are consistent with the presence of VP1 on the surface of the capsid structure. Only VP1-containing capsids allow production of neutralizing antibodies in rabbits. Individual human convalescent phase antisera and pooled immunoglobin recognize mainly VP1 rather than VP2, even though the main acid sequence of VP2 is entirely contained within VP1; antisera that recognize predominantly VP1 are equivalent to antisera that recognize VP2 in their ability to neutralize virus (*J. Clin. Invest.* 84:1114–1123 (1989)). VP1's unique region of 228 amino acids contains at least one neutralizing epitope by peptide mapping.

The minor structural protein appears to be more immunogenic than the major protein. For example, most convalescent sera, that is sera from people who have been exposed to the virus previously, recognize predominantly the minor structural protein. The minor structural protein may be the binding site for the receptor. Empty capsids having a higher minor structural protein to major structural protein ratio are useful for immunization as the number of neutralizing sites is increased.

In a preferred embodiment, capsids enriched with the minor structural protein are produced by altering the relative amounts of VP1 and VP2 containing baculoviruses, so that the ratio of VP1 to VP2 is between 10:1 to 100:1.

In another embodiment, the present invention relates to a safe and effective method of producing antibodies against parvovirus capsids. The method comprises immunizing a mammal with the non-infectious, empty parvoviral capsids described above comprising the major and the minor structural proteins, using protocols known in the art, and isolating the antibodies produced. Monoclonal antibodies specific for the parvoviral capsid can also be produced and isolated using known techniques. In a preferred embodiment, the antibodies, or useful binding fragments thereof, are specific for an epitope present on the B19 capsid.

In another embodiment, the present invention relates to a vaccine effective against parvoviral infection. The vaccine includes the empty, non-infectious capsids described above (or an immunogenically effective portion thereof), purified so as to be essentially free of other proteins (that is, so as to be safe for use as a vaccine). The capsids are preferably, composed of both the minor and the major structural proteins since neutralizing antibodies are elicited by capsids containing the minor structural protein and are not elicited by capsids containing only the major structural protein. In a preferred embodiment, the capsids are B19 capsids. Naturally VP1 accounts for 3–5% of the protein in virion. VP1 also accounts for about 3–5% of the protein in capsids produced in host cells coinfected at a ratio of 1:1 with baculoviruses encoding VP1 and baculoviruses encoding VP2. When host cells are coinfected at a ratio of between 10:1 and 100:1 with baculoviruses encoding VP1 and baculoviruses encoding VP2, the amount of VP1 is increased to 25–30% of the capsid proteins (see FIG. 13).

The invention also relates to diagnostic assays and kits based thereon for detecting the presence in a biological sample of either parvoviral antigens or antibodies thereto. When parvoviral antigens are sought to be detected, antibodies specific for same, produced as described above, can be used according to known protocols to effect antigen detection. When antibodies are sought to be detected, the above-described empty, non-infectious parvoviral capsids (or portions thereof recognized by the antibody), can be used as the antigen, in accordance with known techniques. Capsids containing the minor and the major structural proteins as well as capsids containing only the major structural protein can be used as the antigen. It is contemplated that immunodeficient individuals incapable of producing antibodies against parvovirus can be detected by challenging such individuals with the empty, non-infectious capsid containing the minor structural protein described above and determining whether antibody is produced in response to the challenge.

The diagnostic kits of the invention comprise the above-described antibodies (or binding fragments) and/or capsid antigens and reagents, such as ancillary agents, for example, buffering agents. Where necessary, the kit can further include members of a signal-producing system, numerous examples of which are known in the art.

In another embodiment, the present invention relates to methods for packaging and delivering genetic material to the genome of a cell. The method comprises encapsidating the genetic material sought to transferred into the empty, non-infectious parvoviral capsid described above containing the minor and the major structural proteins, and introducing the capsid into a host cell under conditions such that, once inside the cell, the genetic material is released from the capsid and expressed. In a preferred embodiment, adenoassociated virus DNA is used as that vector system. (See Lebkowski et al. *Mol. Cell. Biol.* 8:3988 (1988) and McLaughlin at al. *J. Virol.* 62:1963 (1988)).

Genetic material suitable for use in such a method includes genes encoding proteins useful in the treatment of genetic defects, for example, hemoglobinopathies and enzyme deficiency states. Host cells include, for example, mammalian stem cells.

Figure 14A:
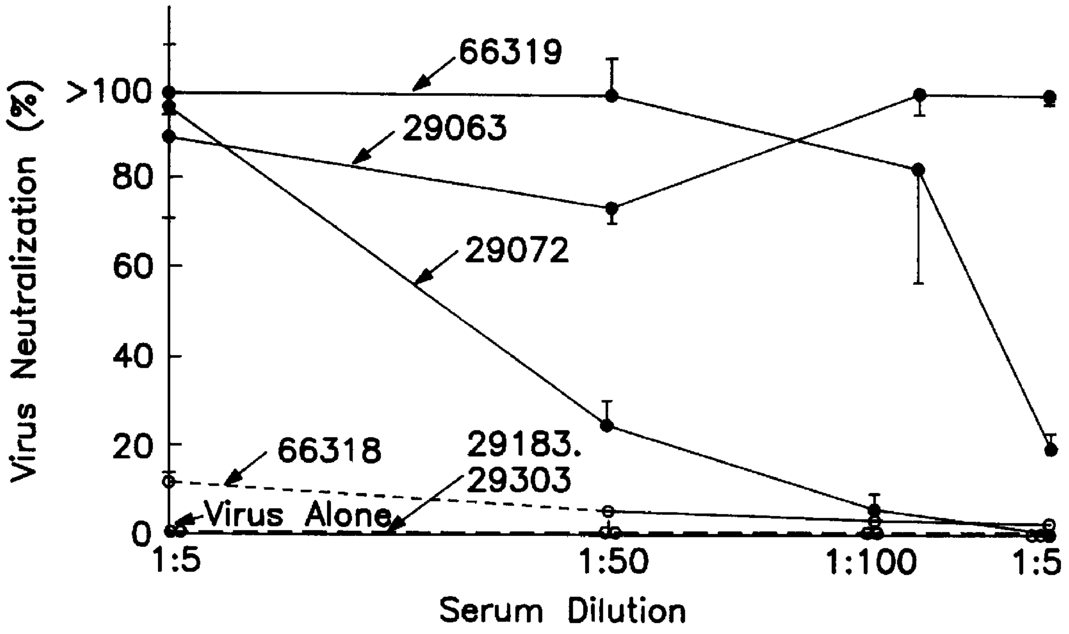
FIGS. 14A–14B. Neutralization of B19 parvovirus infectivity for human erythroid progenitors. Sera from six rabbits immunized with partially purified capsids composed of VP2 alone or VP2 and VP1 were tested for their ability to abrogate the toxic effect of B19 parvovirus in bone marrow cultures.
Figure 14B:
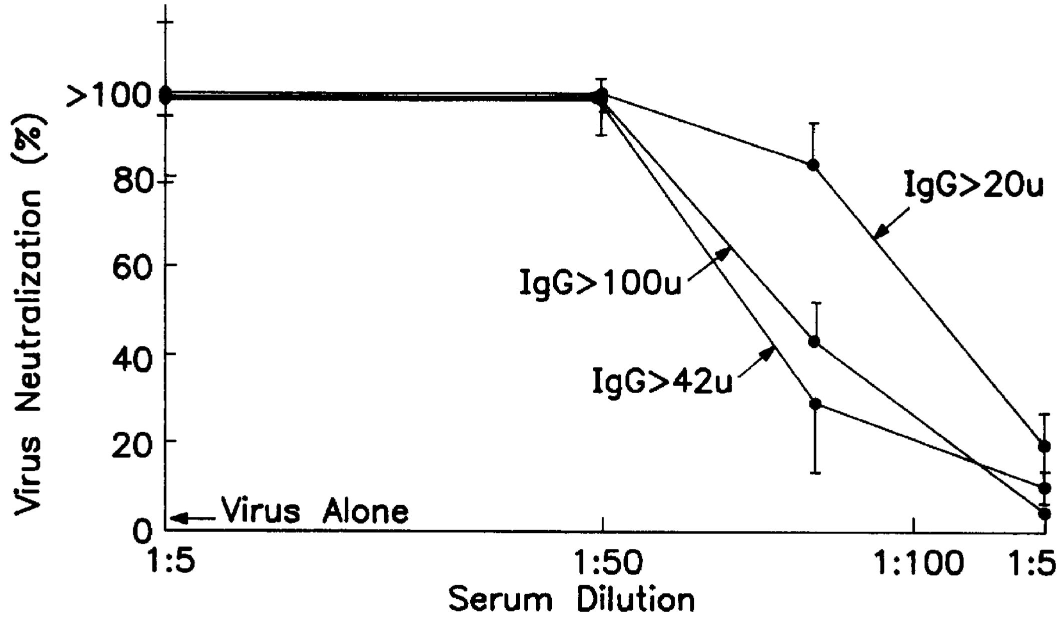
Figure 15A:
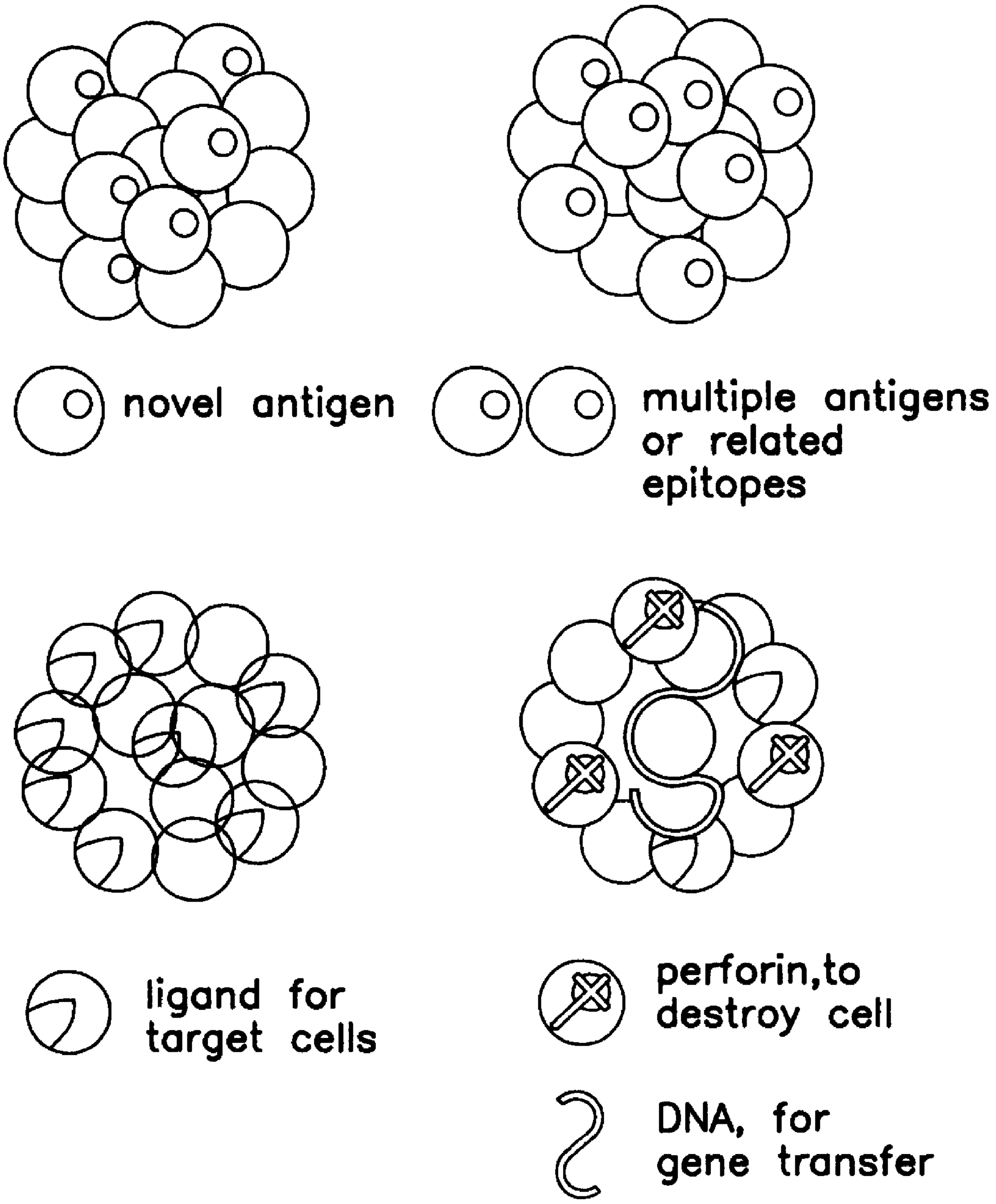
FIGS. 15A–15B. Schematic representation of a protein presenting capsid.
Figure 15B:
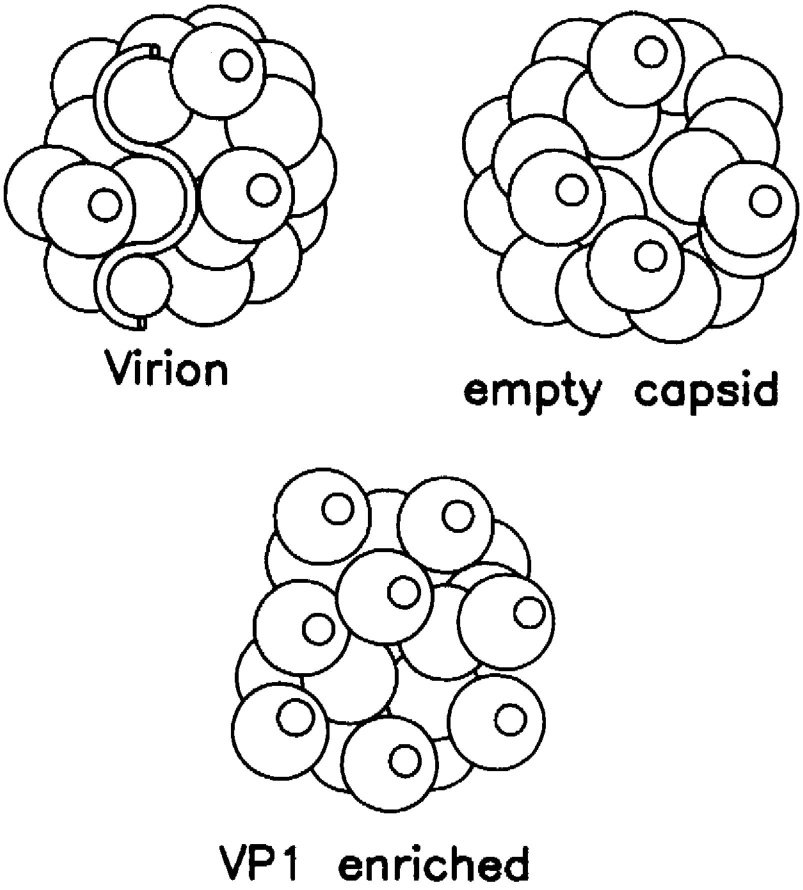

In another embodiment, the present invention relates to a method of producing a protein presenting capsid (see FIG. 14). Protein presenting capsid can be made by substituting nonparvovirus proteins, such as, antigenic epitopes, ligands, enzymes or peptide sequences, for the unique region of the minor structural protein (e.g., VP1). (The unique region of VP1 contains amino acids 1–226.) Recombinant baculoviruses encoding the modified minor structural protein can be produced using methods known in the art. The recombinant baculovirus can then be used to coinfect an insect cell together with a recombinant baculovirus encoding the major structural protein to effect self-assembly of a parvovirus capsid having nonparvovirus proteins expressed on the surface thereof. Such capsids can be used for example, to present antigenic epitopes for vaccination purposes.

Epitopes which can be substituted for the unique region of VP1 include, for example, vaccine epitopes, such as diphtheria or pertussis epitopes. Further, capsids expressing multiple epitopes (for example, pertussis and B19 and diphtheria), can be generated using multiple recombinant minor structural protein genes. The use of such capsids in vaccines eliminates the use live vaccine and therefore related complications.

In addition, the unique region of the minor structural protein can be replaced with a ligand for a cell surface receptor or an enzyme. Capsids including ligand proteins can be targeted to certain cells. For example, capsids expressing a portion of a growth factor molecule would only bind to cells that had a receptor for that molecule. Capsids of the present invention can also be used to deliver enzymes to the circulation system to treat diseases. As it is contemplated that different proteins can be expressed on a single capsid surface, enzymes that attack, label or destroy cells (for example, performs which poke holes in cells), can be combined with ligands that target the capsid to a cell to effect efficient cell killing or labeling. Such capsids can be used as general delivery system for proteins.

The protein presenting capsids of the present invention can also be used in vitro as well as for therapeutic treatment. For example, the protein presenting capsids can be used in assays, such as immunoassays for the detection of antibodies to various proteins.

The following non-limiting Examples describe the invention in more detail.

EXAMPLE I

Preparation of Recombinant DNA Molecules and Transfection of CHO Cells

The DHFR minigene employed consisted of the entire encoding region of the DHFR gene and included the first intron; this construct was derived by restriction enzyme digestion and ligation from that original DHFR minigene, DM-1 (*Molec. Cell. Biol.* 7:2830, 1987). The promoter-enhancer and polyadenylation signals were derived from the SV40 virus. For transfection, the DHFR minigene was cloned in pUC19 (see FIG. 1).

Figure 2:
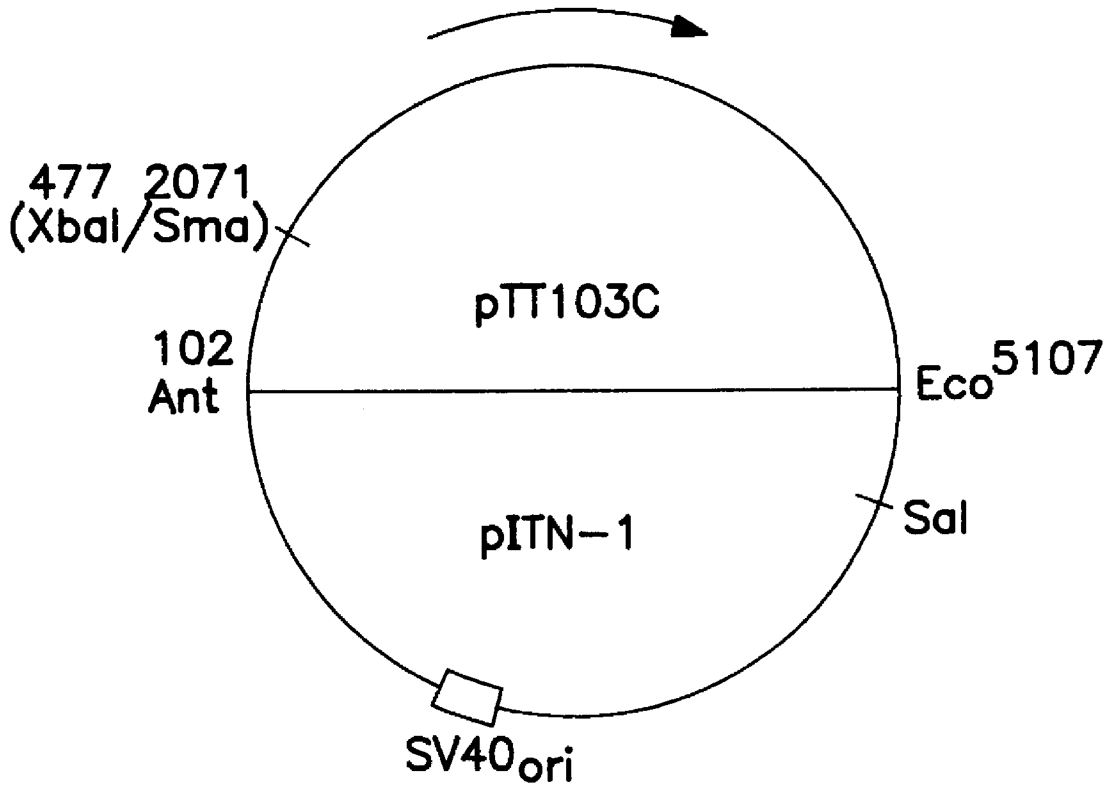
FIG. 2. Structure of the B19 capsid expression vector.

To prepare the B19 capsid expression vector, the nearly full-length B19 genomic clone pYT103c was digested with the enzymes EcoR1 and Aat and subcloned into the standard vector pLTN-1. The nonstructural region was deleted by digestion with Xba1 and Sma1 enzymes and recircularized (see FIG. 2).

CHO cells were cotransfected with DNA from two plasmid constructs, one containing the DHFR minigene and the other containing the B19 capsid genes. Transformants bearing the DHFR+ phenotype were selected by growing the cells in medium lacking nucleosides and colonies were screened by RNA Northern analysis for expression of B19 genes. Coamplification of the integrated B19 capsid encoding sequence and the DHFR sequence was accomplished by treating the cells with increasing concentrations of methotrexate. 3-11-5 is a cell line established as described above which expresses the B19 capsid.

EXAMPLE II

DNA and RNA Analysis

Figure 3:
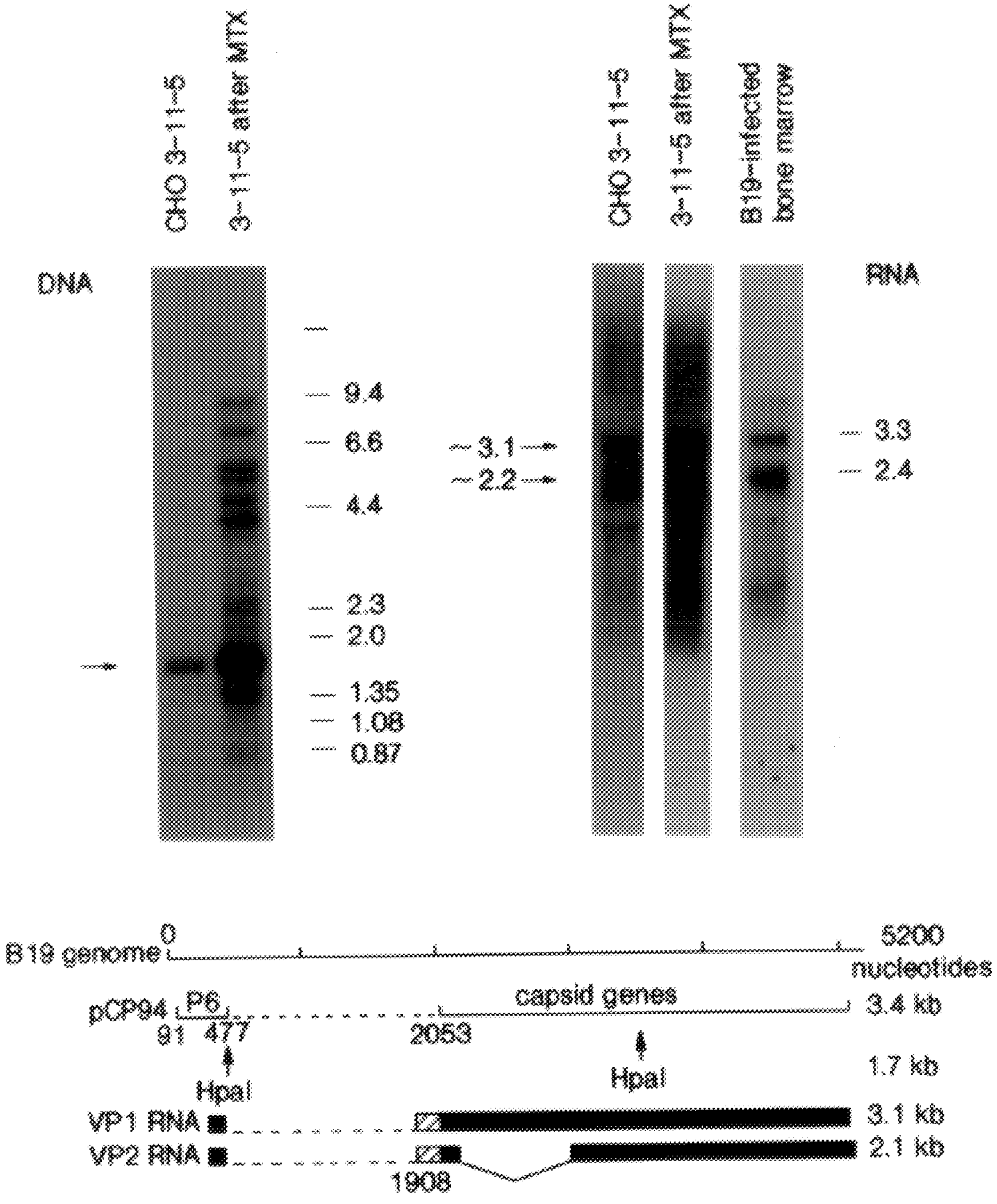
FIG. 3. Amplification of B19 capsid genes.

DNA was prepared by conventional phenol-chloroform extraction and proteinase K digestion and RNA by the conventional guanidinium sulfate method from 3-11-5 cells before and after culture in increasing concentrations of methotrexate (final concentration =10 $\mu$M). DNA was analyzed by Southern and RNA by Northern hybridization using pYT103c, a B19 specific labeled DNA probe (*Science* 233:883 (1986)). The migration on agarose gel electrophoresis of the B19 DNA from 3-11-5 cells is consistent with the size of the transfected DNA insert and that of the RNA with the transcripts expected from the right side of the virus genome (*J. Virol.* 61:2395 (1987)) (see FIG. 3).

EXAMPLE III

Figure 4:
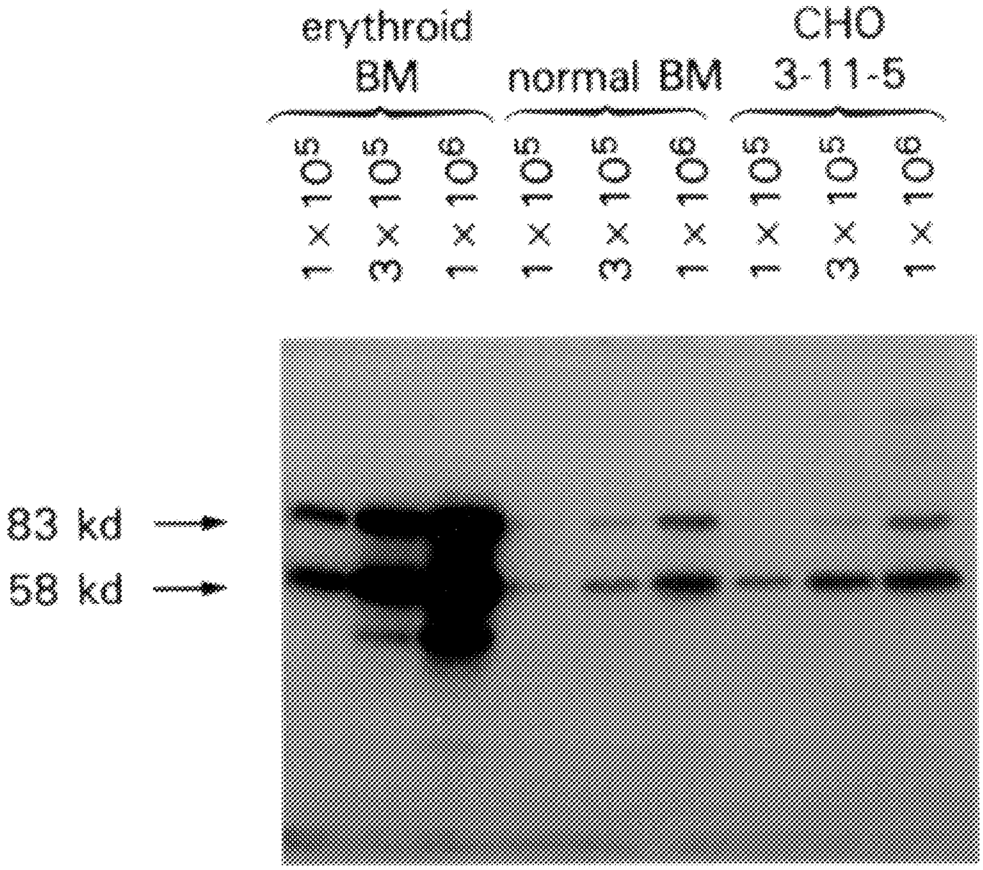
FIG. 4. Immunoblot of B19 capsid proteins in CHO and bone marrow cells.

Comparison of B19 Capsid Accumulation by Immunoblot 3-11-5 cells were compared to normal or erythroid bone marrow cells inoculated with virus and harvested at 48 hours (the peak of virus production; *Blood* 70:384 (1987)). Capsid protein was detected by Western blot using convalescent phase antiserum containing high titer anti-B19 capsid protein IgG (J. Virol. 61:2627 (1987)) (see FIG. 4). The amount of 58 kd and 83 kd protein in 3-11-5 cells was intermediate between that harvested from cultures of normal and erythroid bone marrow. From comparison to known standard plasma preparations, it has been estimated that each 3-11-5 cell contains between 1000–20000 capsids.

EXAMPLE IV

Figure 5A:
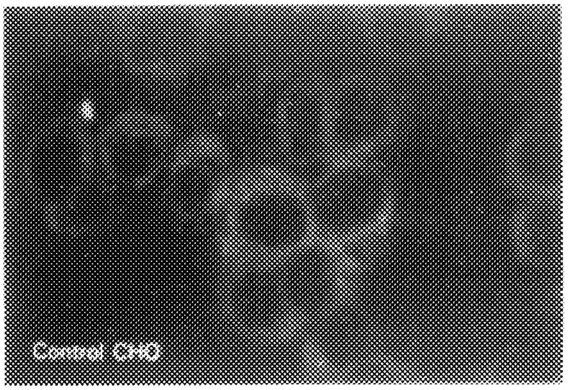
FIGS. 5A–5B. Immunofluorescence of a capsid-producing Chinese hamster ovary (CHO) cell-line.
Figure 5B:
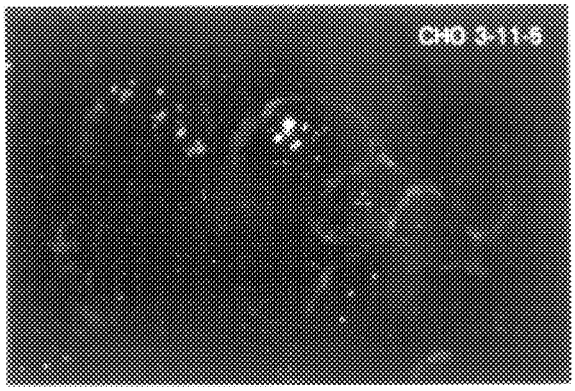

Immunofluorescence 3-11-5 and control CHO cells ware fixed with acetone and stained with human convalescent phase serum containing anti-B19 capsid antibodies followed by fluorescein-conjugated anti-human IgG (*J. Clin. Invest.* 74:2024 (1984) ). All 3-11-5 cells show a pattern of strong and specific immunofluorescence in both cytoplasm and nuclei (see FIG. 5).

EXAMPLE V

Sedimentation Analysis of Capsids from 3-11-5 Cells

Figure 6A:
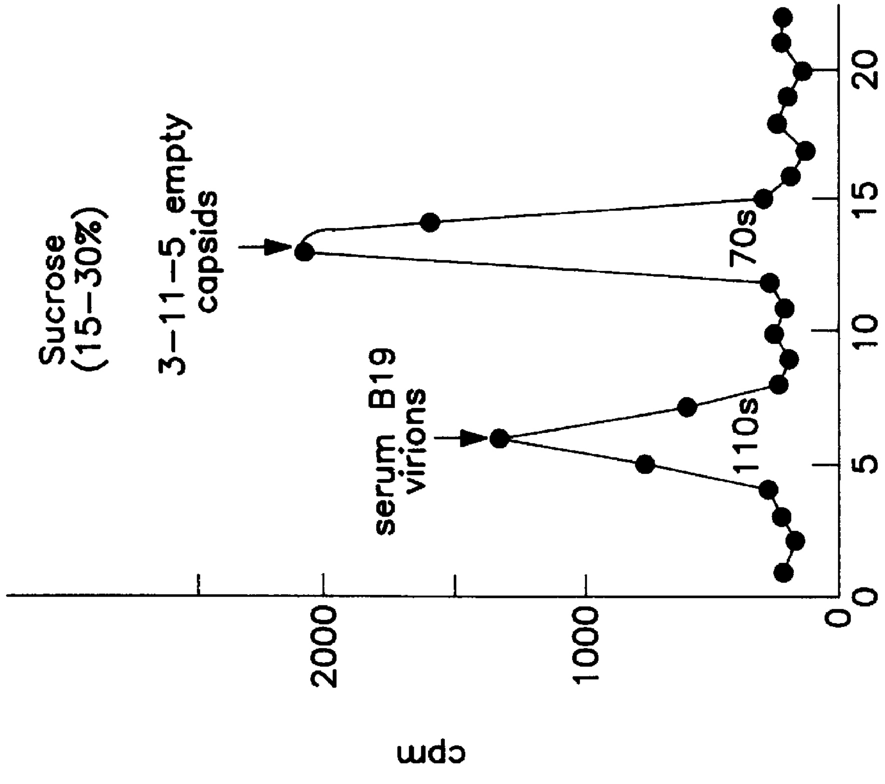
FIGS. 6A–6B. Sedimentation of B19 capsids.
Figure 6B:
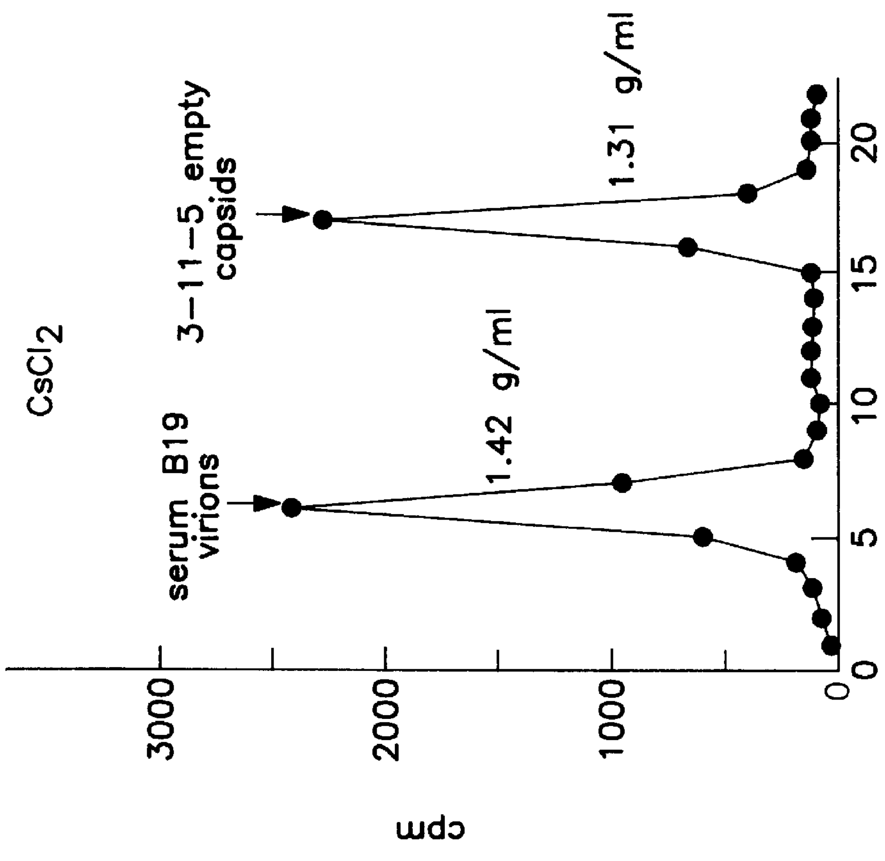

Capsids from CHO 3-11-5 cells were compared to viral particles from human bone marrow culture *Blood* 70:385 (1987)). Proteins were labeled by exposure of cultures to 35S-methionine, the cells were lysed, and the particulate fraction obtained by centrifugation over a 40% sucrose cushion (*J. Virol.* 61:2627 (1987)). After suspension of the particulate fraction in a small volume of buffer, radioactively labeled capsids or virions were applied to sucrose (*J. Clin. Invest.* 73:224 (1984)) or cesium chloride (*Science* 233:883 (1986)) gradients (see FIG. 6). On sucrose gradient sedimentation, empty capsids were clearly distinguished from intact virions, and isopycnic sedimentation in cesium showed a density consistent with empty capsids.

EXAMPLE VI

Electron Microscopy of 3-11-5 Cells

Figure 7:
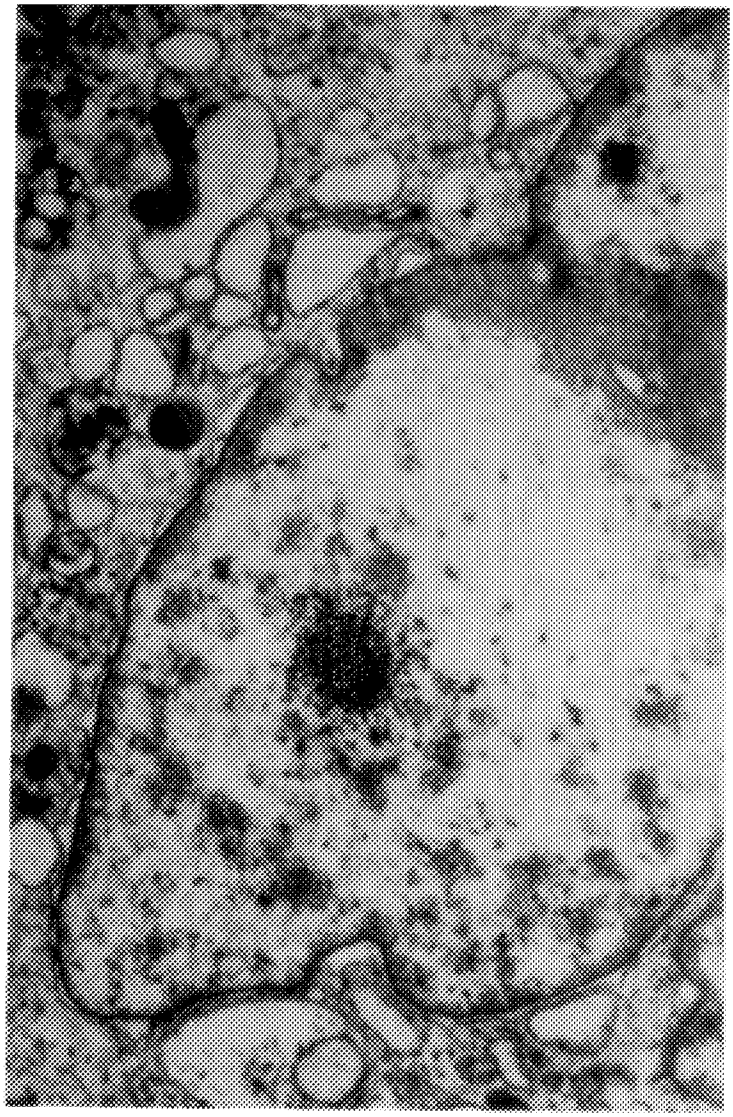
FIG. 7. Electron micrograph of transformed CHO cells—demonstration of intranuclear viral particles.

Cells were fixed and prepared for transmission EM as described (*J. Clin. Invest.* 74:2024 (1984)). Characteristic clusters of 20 nm particles were observed in the nuclei of 3-11-5 cells only (see FIG. 7).

EXAMPLE VII

Growth Curves of 3-11-5 Cells Compared to Other CHO Cells

Figure 8:
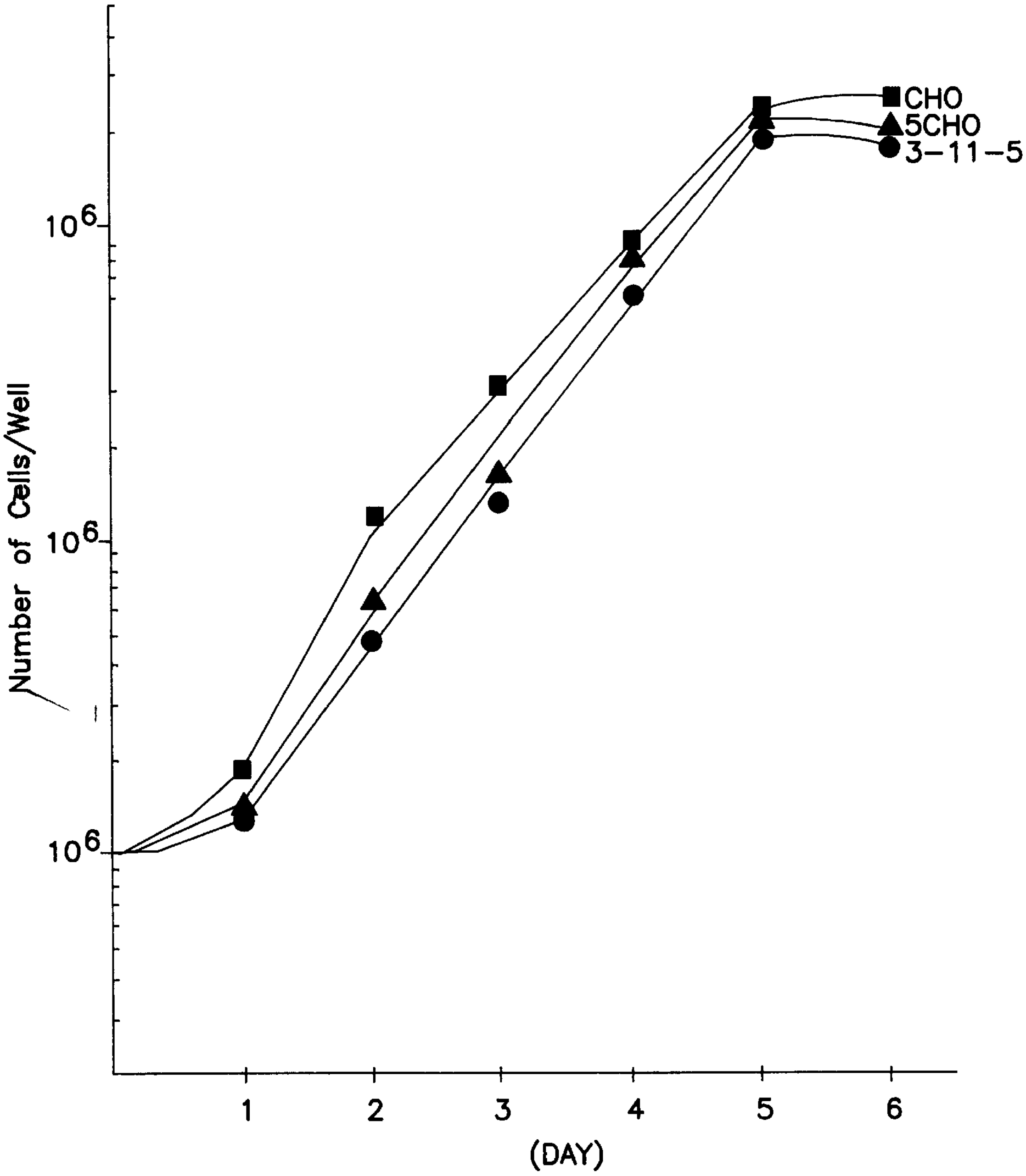
FIG. 8. Growth curves.

Cells were serially harvested from microtiter wells and manually counted. Empty capsid production does not adversely affect cell proliferation of 3-11-5 (see FIG. 8).

EXAMPLE VIII

Preparation of Recombinant Baculoviruses, Transfection of Sf9 Cells and Expression of Capsids Cell culture and virus stocks were prepared as follows. Recombinant plasmid was used to generate recombinant baculoviruses. Autographa california nuclear polyhedrosis virus (AcMNPV) and recombinant polyhedrosis viruses were grown in monolayers of Sf9 cells. The Sf9 cell line (American Type Culture Collection, Rockville Md.), which is derived from Spodoptera frugiperda (fall army worm) ovary, was maintained in Grace's insect tissue culture medium containing 10% heat inactivated fetal bovine serum, 2.5 μg/ml fungizone, 50 μg/ml gentamicin, 3.33 mg/ml lactalbumin hydrolysate, and 3.33 mg/ml yeastolate (provided complete by Gibco BRL Life Technologies, Gaithersburg Md.) at 100% room air, 95% humidity, at 27° C.

Recombinant plasmids and recombinant baculoviruses were constructed as follows. Two plasmids were constructed, one containing the full length major capsid protein gene (VP2), the other the full length minor capsid protein gene (VP1). To construct plasmid pVP1/941, a CDNA encoding the VP1 gene was excised from pYT103c, a nearly full length molecular clone of B19 parvovirus (Cotmore et al. *Science* 226:1161 (1984); Ozawa et al. *J. Virol.* 62:2884 )1988)), by digestion with the restriction enzymes Hind III (which cuts at map unit 45) and EcoRI (which cuts at map unit 95) followed by treatment with mung bean nuclease to complement single stranded ends.

Figure 9A:
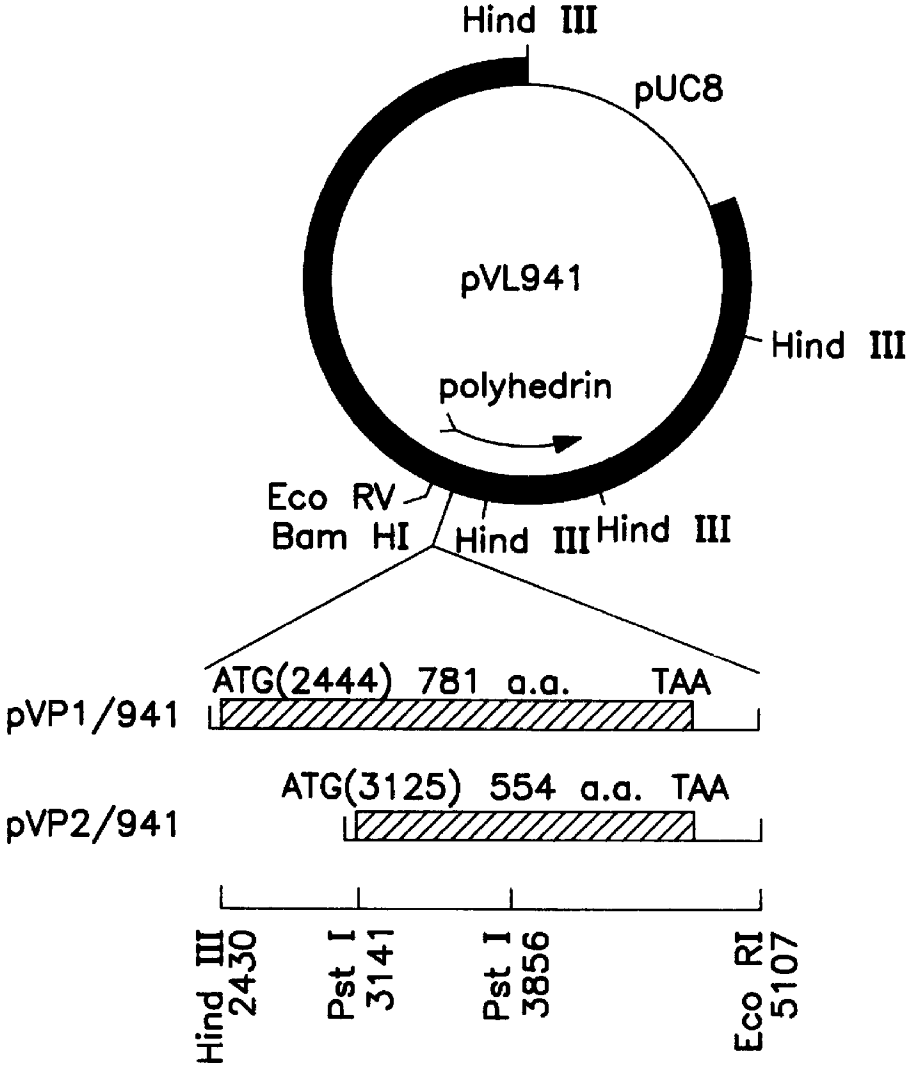
FIGS. 9A–9B. Plasmid constructions containing the major (VP2) and minor (VP1) capsid genes of B19 parvovirus. (A) Diagram outlining relationship of inserts derived from pYT103c, a nearly full-length molecular clone of parvovirus B19, and the baculovirus vector pVL941; (B) synthesized regions of DNA used to complete the gene sequences.
Figure 9B:
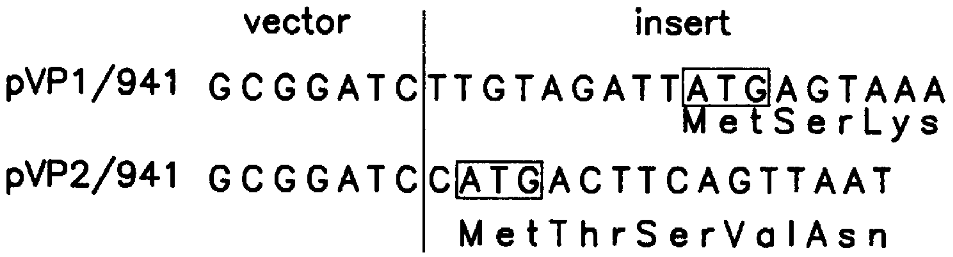

The resultant DNA fragment was inserted into the BamHI site (made blunt ended with the Klenow fragment of DNA polymerase) of the baculovirus transfer vector pVL941, a vector derived by deletion of the polyhedrin gene of AcMNPV followed by cloning into the pUC8 plasmid (Summers et al. *Tex. Agric. Exp. Stn.* 1555 (1987)). Construction of pVP2/941 was performed by the insertion of a PstI-EcoRI digestion fragment of pYT103c (map units 58-95; the EcoRI site was blunt-ended) and a synthetic DNA fragment of 20 nucleotides corresponding to the SstI-PstI region (again with the SstI site blunt-ended) into the BamHI site of pVL941 (FIG. 9).

Recombinant plasmids were used to generate recombinant baculoviruses. Eight μg of each of the recombinant plasmids was cotransfected into Sf9 cells with 2 μg of wild type AcMNPV, using calcium phosphate-mediated precipitation. Six days after transfection, progeny virus was harvested and replaqued onto fresh Sf9 cells. Recombinant viruses were recognized visually by the absence of occlusion bodies in the nucleus of cells (the occlusion-positive phenotype is the result of synthesis of large quantities of the polyhedrin protein). Recombinant viruses were subjected to three cycles of plaque purification before large scale virus stocks were prepared.

For analysis of protein expression and capsid structure, Sf9 cells were infected with recombinant viruses at multiplicity of infections (m.o.i.) ranging from 10 to 50. Cells were harvested and examined for expression of VP1 and VP2 at variable times after infection; four days post-infection was judged optimal for recombinant protein expression. Cytocentrifuge preparations (approximately $1\times10^5$ cells/slide well) of recombinant (VP1–VP2 baculovirus) or wild type virus-infected cells were fixed in acetone at −20° C. for 30 seconds, washed twice in phosphate buffered saline (PBS) containing 0.5% bovine serum albumin, and blotted dry. Cells were stained with convalescent phase human anti-B19 parvovirus antiserum (diluted 1:20), followed by application of fluorescein isothiocyanateconjugated goat antihuman IgG (diluted 1:50: Kierkegaard and Perry, Gaithersburg, Md.).

All cells stained specifically with the human convalescent phase human antiserum, with bright fluorescence observed over cytoplasm and nuclei of fixed cells (FIG. 10); the fluorescent signal was maximal 3–4 days after infection and had faded after one week of culture, at which time most of the cells were no longer viable.

For analysis of proteins by gel electrophoresis, lysates from 4 day old cultures were prepared by heat disruption at 100° C. for 3 minutes in 100 ∞l of Laemmli sample buffer (*Nature* 227:680–685 (1970)). Aliquots of each sample were applied to 8% polyacrylamide gels (10 $\mu$l/lane) in the presence of sodium dodecyl sulfate as described by Laemmli. Proteins were directly visualized by staining with visualized by staining with 0.25% Coomassie brilliant blue dye. For immunoblotting, proteins were transferred by eletroblotting onto nitrocellulose membranes (Hoeffer Scientific, San Francisco Calif.). Specific proteins were detected by sequential application of convalescent phase human antiserum (diluted I:300) and $^{125}$I-labeled protein A (Amersham, Arlington Heights Ill.) by the BLOTTO method (*GeneAnal. Tech.* 1:3–8 (1984)).

Figures 1, 10A:
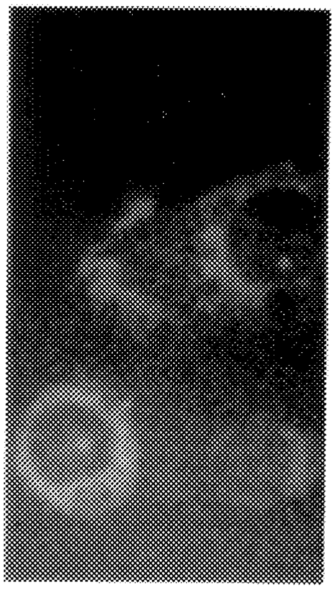
Figures 2, 10A:
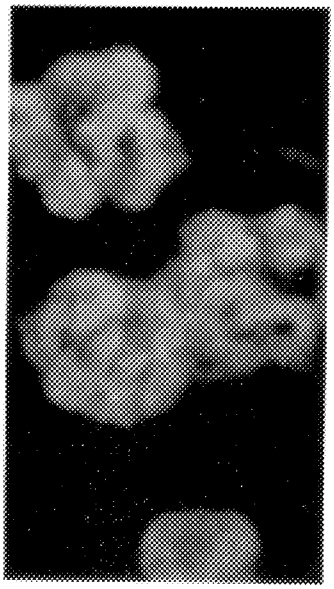
Figures 3, 10A:
Figure 10B:
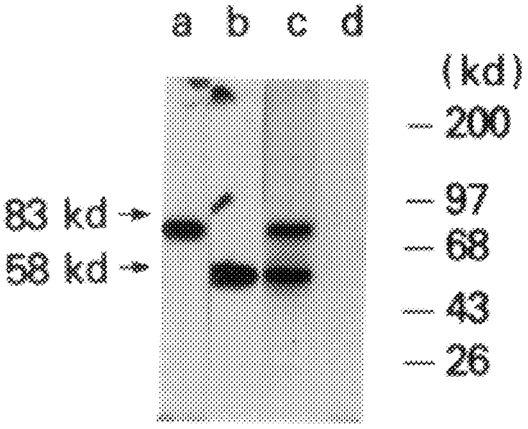
Figure 10C:
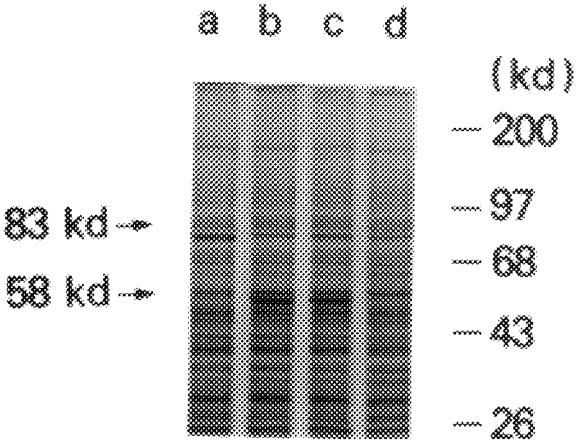

Bands of the appropriate molecular weight were detected after infection with the VP1-baculovirus (FIG. 10B, lane a), VP2-baculovirus (FIG. 10B, lane b), or after coinfection with both recombinant viruses (FIG. 10B, lane c). Large enough quantities of parvovirus structural proteins were produced to be visible after dye staining of polyacrylamide gels of lysates (FIG. 10C); parvovirus protein was estimated by densitometry to constitute 2–3% of total cell protein present.

Capsids were examined by electron microscopy after equilibrium density gradient sedimentation. Sf9 cells were harvested 4 days after inoculation with recombinant baculoviruses (VP1 alone, VP2 alone, or VP1 plus VP2). Lysates were centrifuged at 100,000 ×g over 40% (wt/vol) sucrose in Hank's balanced salt solution. Precipitates were mixed with CsCl in 50 mM Tris-HCl, pH 8.7, 5 mNM EDTA, and 0.1% sarcosyl at an initial density of 1.31 gr/ml, centrifuged at 100,00 ×g in an SW41 rotor for 35 hrs at 18° C. Transmission electron microscopy was performed after three such banding-procedures.

Banding of parvovirus proteins (determined by immunoblot and immunoprecipitation) was detected at 1.31 gr/ml, the appropriate density for empty capsids, for cells infected with VP1-baculovirus and cells coinfected with VP2 and VP1-baculoviruses. No parvovirus protein was detected in cell lysates from VP1-baculovirus infected cells.

Direct electron microscopy was done on pellets after ultracentrifugation of 50 $\mu$l of the sample in 3.5 ml Dulbecco A PBS. Immune electron microscopy was performed by incubating 50 $\mu$l of human serum containing IgG antibody to B19 parvovirus for 45 minutes at 20° C. prior to dilution in PBS and ultracentrifugation. Pellets after centrifugation were resuspended in 50 $\mu$l of distilled water and negatively stained using 3% phosphotungstic acid, pH 6.5. Grids were examined at 60,000 ×magnification in Jeol 1200EX electron microscope. Magnifications were calibrated with catase.

Figure 11A:
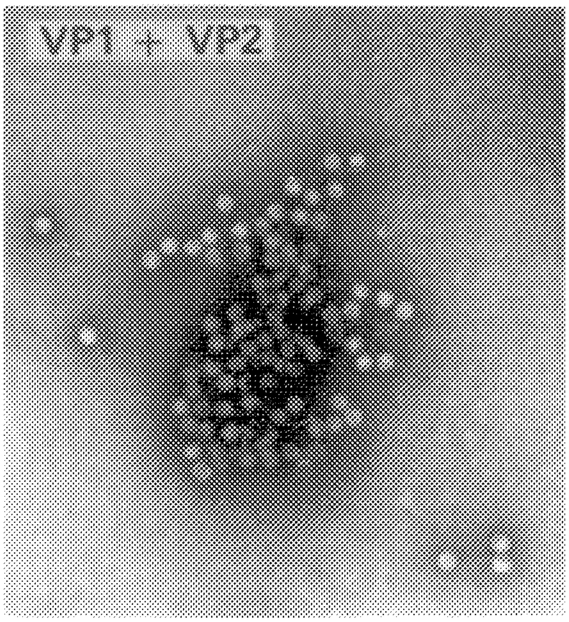
FIGS. 11A–11B. Electron micrographs of empty capsids. After infection with either pVP1/941 plus pVP2/941 or pVP2/941, cell lysates were subjected to equilibrium density gradient sedimentation and examined by transmission electron microscopy after negative staining (x 171,000).
Figure 11B:
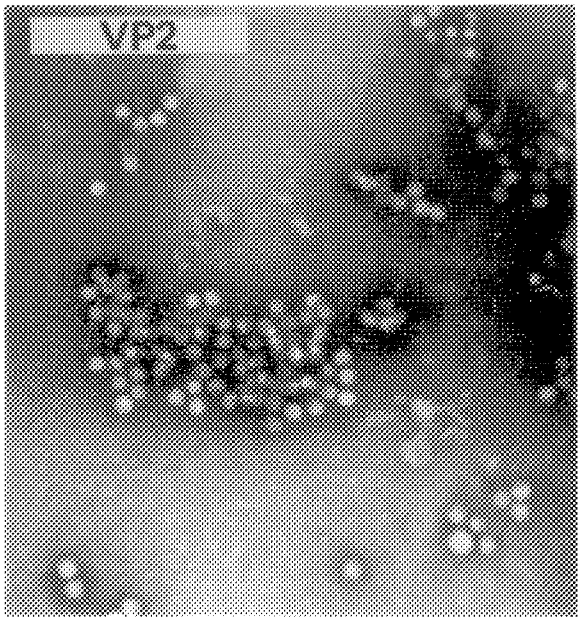

Immune electron microscopy showed typical empty parvovirus capsids, aggregated by the B19 antibody, in samples from cultures coinfected with VP1 and VP2-containing baculoviruses and also in cultures after infection only with VP2-baculoviruses (FIG. 11). No virus particles were seen in lysates of cells infected with VP1-containing baculovirus alone. Direct electron microscopy of harvests from cultures coinfected with VP1 and VP2-containing baculoviruses and from cultures infected with VP2-containing virus only revealed numerous typical parvovirus-like particles that were not coated with antibody. A minority of the particles were electron dense, the majority were less dense, and some particles had intermediate density. Particles tended to cluster together.

The capture immunoassay was adapted from a previously published Elisa immunoassay procedure (*J. Clin. Microbiol.* 24:522–526 (1986)). Capture antibody, either goat anti-human IgG or IgM antibodies (Tago, Burlingame Calif.) was added to 96 2311-microtiter plates (Immunolon, Dynatech, Alexandria Va.) and incubated for 1 hour at 37° C.; the plates were washed and human serum specimens (diluted 1:100) were added for 1.5 hours at 37° C. After washing, positive and control antigens were added overnight at room temperature; antigens included pooled sera from viremic human specimens and baculovirus-expressed antigen. Further washing of the plates to remove antigen was followed by addition of biotinylated monoclonal antibody (MAb 521-5d, diluted 1:2000) for 1 hour at 37° C., another wash step, and addition of peroxidase-conjugated streptavidin (plc, Amersham International, United Kingdom) for 10 minutes at room temperature. Substrate for the enzyme (0.1 mg/ml of 3,3'5,5'-tetramethyl-benzidine and 0.005% $H_2O_2$ in dimethyl sulfoxide and acetate-citrate buffer, pH 5.5) was added to the plates after further washing for 15 minutes at room temperature; the reaction was stopped with 2M $H_2SO_4$ and the absorbance at $A_{450}$ determined. Capture antibody was diluted in 0.01M carbonate buffer, pH 9.6; other reagents were diluted in phosphate buffered saline (pH 7.2) with 0.5% gelatin and 0.15% Tween-20; plates were washed with phosphate buffered saline, 0.15% Tween-20.

Each serum specimen was tested in duplicate against baculovirus antigen and negative control antigen at 1:2000 dilution and against a human serum pool of viremic blood at a dilution of 1:200. A serum specimen was considered positive in the baculovirus IgG immunoassay if the P-N was >0.35 and the P/N ration was >2.0, in the baculovirus IgM immunoassays if P-N was >3.0 and P/N was >2.0, and in the human serum IgG and IgM immunoassays if P-N was >3.0 and P/N was >2.5. P is the mean absorbance for the serum specimen reacted against the B19 viral antigen less mean absorbance due to nonspecific binding of B19 viral antigen (negative serum or diluent reacted against positive antigen minus negative serum reacted against control antigen). N is the mean absorbance for the same serum specimen reacted against the respective negative control antigen. These values of P-N and P/N are ≧3 standard deviations above the mean values for specimens previously determined to be antibody-negative.

Figure 12A:
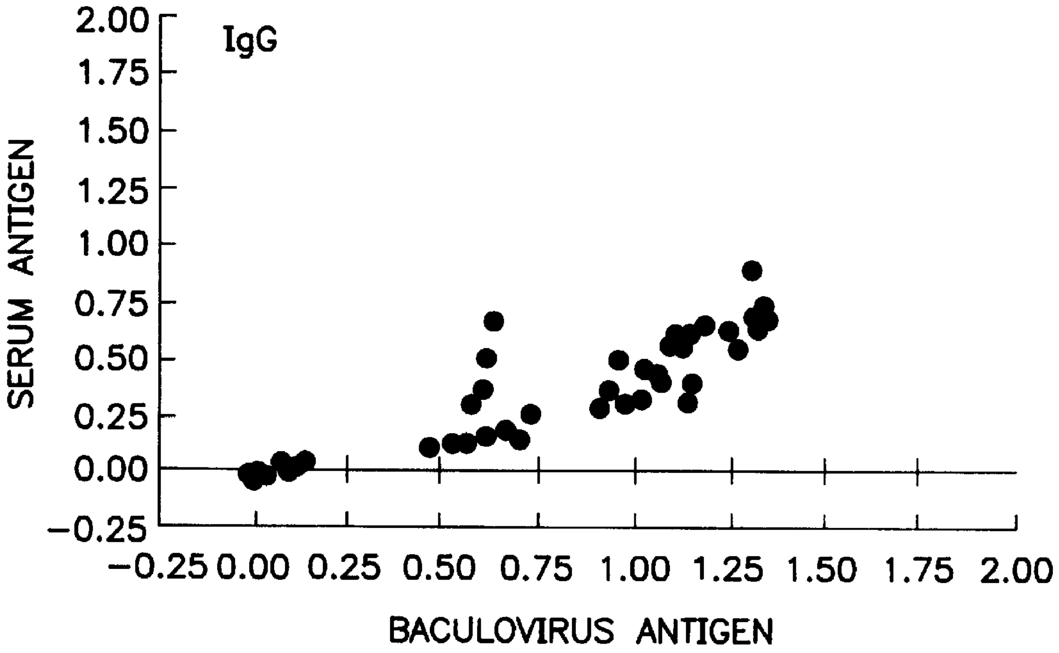
FIGS. 12A–12B. Capture immunoassay comparing antigen derived from serum of infected patients with Sf9 c311 lysate after in vitro infection with pVP2/941.
Figure 12B:
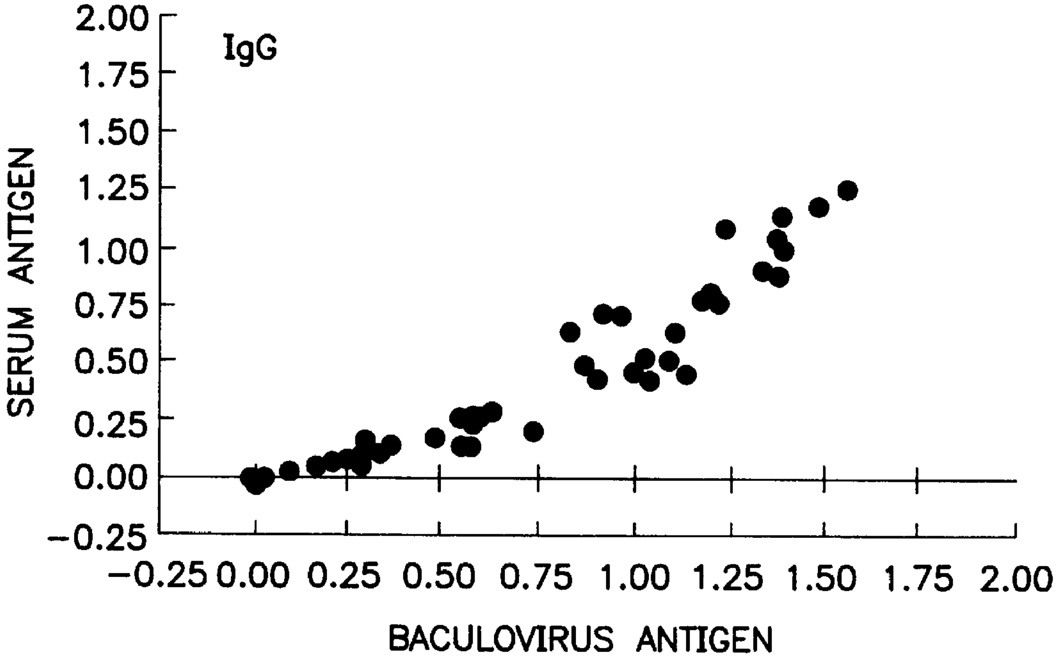
Figure 13A:
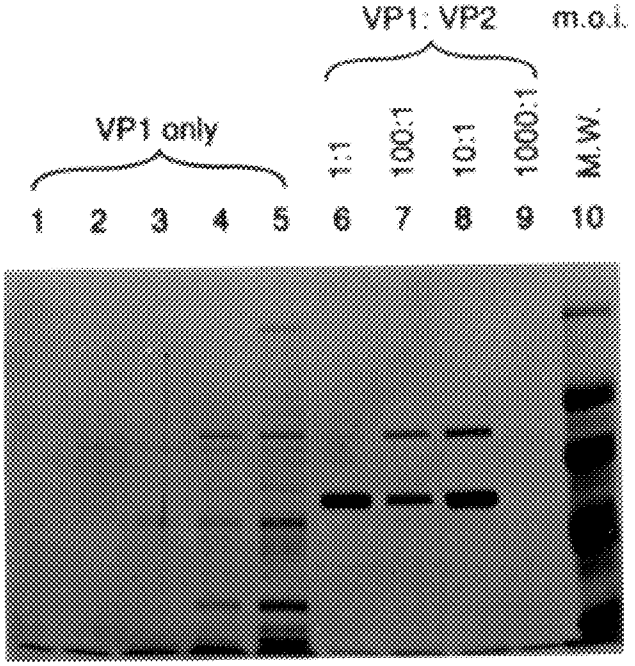
FIGS. 13A–13D. Shows supernormal amounts of VP1 were present in the recombinant capsids when the relative multiplicity of infection for VP1 and VP2 baculoviruses was increased from 1:1 (7% VP1) to 100:1 (30% VP1). These results have two significant implications. First, because VP1 is immunogenic and probably contains the receptor binding site, a capsid enriched for VP1 compared to virion may be particularly effective as a vaccine reagent because it increases the amount of desirable antigen presented to the immune system. Second, the unique region of the VP1 plasmid could be replaced with other epitopes and other recombinant baculoviruses generated. In this way, the basic capsid structure could be used to present multiple or different antigens to the host (that is, tetanus, gp120 of HIV) in the context a stable, highly immunogenic particulate structure.
Figure 13B:
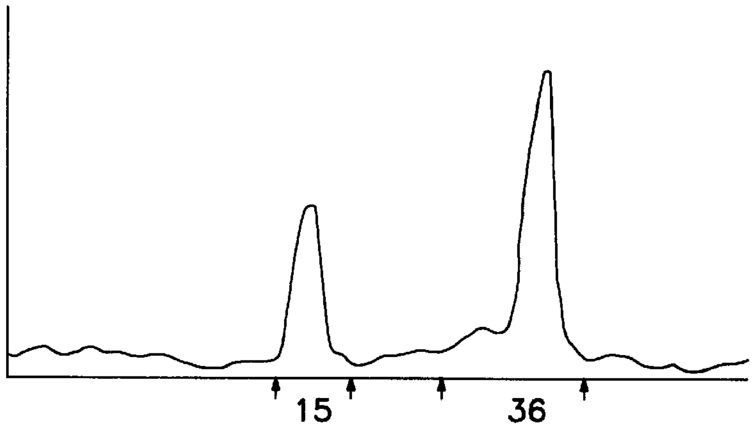
Figure 13C:
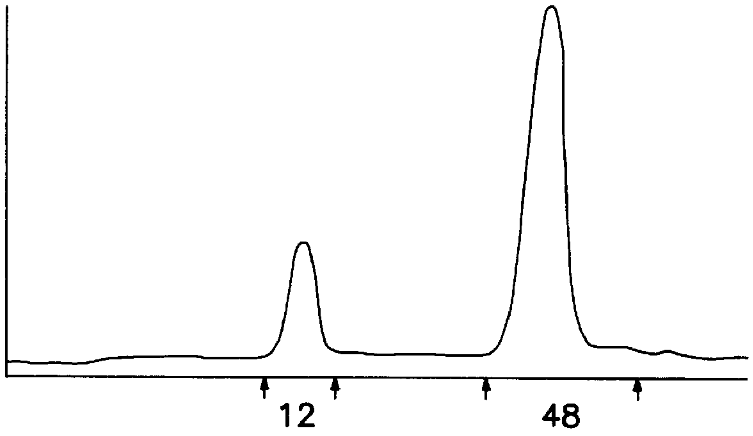
Figure 13D:
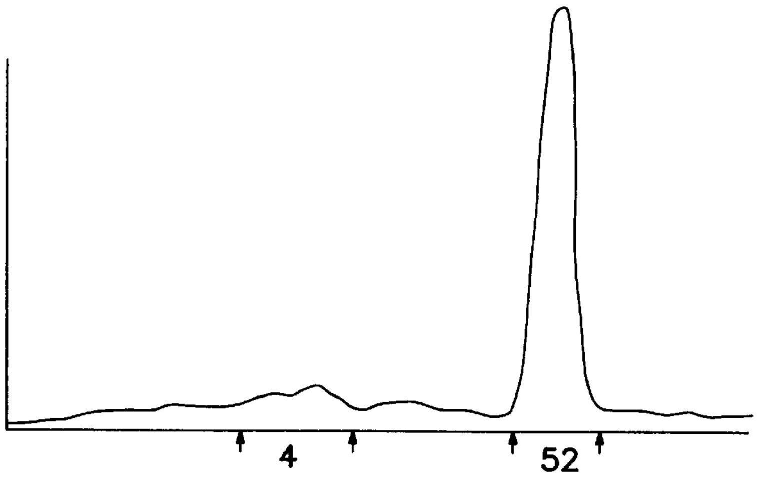

For the IgG assay, 23 specimens were negative in both immunoassays, 45 were positive in both assays, and none was discordant. For the IgM assay, 25 specimens were negative in both assays, and none was discordant. The assays based on the two different sources of antigen also gave comparable qualitative results (FIG. 12). The correlation coefficients for P-N absorbance values for serum antigen versus baculovirus antigen wa 0.95 for the IgG immunoassays and 0.91 for the IgM assay.

For the production of antisera, rabbits were immunized with partially purified empty capsids obtained after coinfection of insect cells with either VP1 and VP2-containing baculovirus or with only VP2-containing baculovirus. After lysis, capsids were subjected to sedimentation over sucrose and in cesium chloride, as described above. Animals were inoculated with either 20 or 200 $\mu$g of capsid protein by subcutaneous injection, initially in complete Freund's adjuvant and with booster injections in incomplete Freund's adjuvant at 2–4 week intervals. Rabbit sera were analyzed by immunoblot and in neutralization assays.

To determine neutralizing activity, sera were heated to 56° C. for 30 minutes to destroy complement activity and incubated at varying concentrations with quantities of B19 parvovirus known to inhibit erythropoiesis in vitro. The inhibitory activity of virus treated with antiserum was compared to virus alone in conventional assays of late erythroid progenitors (CFU-E), cultured in 0.8% methylcellulose containing 30% fetal calf serum, 1% bovine serum albumin, $10^{-3}$ beta-mercaptoethanol, and 1 $\mu$/ml recombinant erythropoietin (Amgen, Thousand Oaks Calif.) at 37° C., 95% humidity for 6–7 days. Control experiments included assay of preimmune rabbit sera and similarly diluted normal human sera that had been obtained from patients in the convalescent phase of parvovirus infection; these sera contained antibody to B19 parvovirus, as determined in the capture immunoassay.

None of the animals inoculated with low doses of antigen (20 $\mu$g/injection) produced neutralizing antisera. However, in 3/3 animals immunized with larger quantities of empty capsids (200 $\mu$g/injection), composed of both VP1 and VP2, obtained after coinfection of insect cells with the two individual recombinant viruses, neutralizing antisera was produced. The titers of neutralizing activity in two animals were comparable to those observed in convalescent phase human sera. (FIG. 14 shows the production of neutralizing antisera in response to capsid containing both VP1 and VP2).

In contrast, none of three sera from animals immunized with VP2-containing capsids produced neutralizing antibody. Ouchterlony analysis was used to determine if precipitating antibodies were made by these animals, using empty capsids made in mammalian cells or VP2-only capsids produced in baculovirus as antigens: sera from the animals which had produced neutralizing antibodies after immunization with VP1 and VP2 also contained precipitating antibodies, and sera from the animals immunized with VP2-capsule also demonstrated precipitating antibodies.

The foregoing invention has been described in some detail by way of examples for purposes of clarity and understanding. It will be obvious to those skilled in the art from a reading of the disclosure that site-directed mutagenesis can be used to alter the amino acid sequence of the above described capsids and thereby alter the tissue specificity of the virus. Furthermore, it will be clear that the DHFR-deficient CHO cells can be used to study the effect of nonstructural parvoviral proteins on cell replication. It will also be apparent that various combinations in form and detail can be made without departing from the scope of the invention.

The entire contents of all published articles cited herein are hereby incorporated herein by reference.

What is claimed is:

1. A diagnostic assay for the presence of antibodies to B19 parvovirus in a sample from a patient suspected of being infected with B19 parvovirus, the assay comprising:

i) contacting the sample with isolated empty B19 parvovirus capsids, and ii) detecting the formation of an antigen antibody complex.

2. The assay of claim 1, wherein the capsids contain VP2 major structural protein and VP1 minor structural protein.

3. The assay according to claim 1, wherein said sample is a serum sample.

4. A diagnostic kit to detect the presence of antibodies to B19 parvovirus, comprising:

i) isolated empty B19 parvovirus capsids, and ii) ancillary reagents.

5. The diagnostic kit according to claim 4, further comprising a signal-producing system.

6. The diagnostic kit according to claim 4, wherein the capsids contain VP2 major structural protein and VP1 minor structural protein.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Parvovirus ( i x ) FEATURE:
( A ) NAME/KEY: CDS
( B ) LOCATION: 17..25

( x i ) SEQUENCE DESCRIPTION: SEQ ID NO:1:

```
GCGGATCTTG TAGATT ATG AGT AAA                                     25
                  Met Ser Lys
                  1
```

( 2 ) INFORMATION FOR SEQ ID NO:2:

( i ) SEQUENCE CHARACTERISTICS:
( A ) LENGTH: 3 amino acids
( B ) TYPE: amino acid
( D ) TOPOLOGY: linear ( i i ) MOLECULE TYPE: protein ( x i ) SEQUENCE DESCRIPTION: SEQ ID NO:2:

-continued

```
Met Ser Lys
 1


(2) INFORMATION FOR SEQ ID NO:3:

     (i) SEQUENCE CHARACTERISTICS:
          (A) LENGTH: 23 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (vi) ORIGINAL SOURCE:
          (A) ORGANISM: Parvovirus

    (ix) FEATURE:
          (A) NAME/KEY: CDS
          (B) LOCATION: 9..23

    (xi) SEQUENCE DESCRIPTION: SEQ ID NO:3:

GCGGATCC ATG ACT TCA GTT AAT                                  23
         Met Thr Ser Val Asn
          1               5


(2) INFORMATION FOR SEQ ID NO:4:

     (i) SEQUENCE CHARACTERISTICS:
          (A) LENGTH: 5 amino acids
          (B) TYPE: amino acid
          (D) TOPOLOGY: linear

    (ii) MOLECULE TYPE: protein

    (xi) SEQUENCE DESCRIPTION: SEQ ID NO:4:

Met Thr Ser Val Asn
 1               5
```